(12) United States Patent
Gehl

(10) Patent No.: US 6,447,541 B1
(45) Date of Patent: Sep. 10, 2002

(54) METHOD FOR MANUFACTURING AN EPITHESIS

(76) Inventor: Gerolf Gehl, Zürichstrasse 56, Küsnacht (CH), CH-8700

( * ) Notice: Subject to any disclaimer, the term of this patent is extended or adjusted under 35 U.S.C. 154(b) by 0 days.

(21) Appl. No.: 09/508,286

(22) PCT Filed: Sep. 9, 1998

(86) PCT No.: PCT/EP98/05756

§ 371 (c)(1),
(2), (4) Date: May 13, 2000

(87) PCT Pub. No.: WO99/12500

PCT Pub. Date: Mar. 18, 1999

(30) Foreign Application Priority Data

Sep. 9, 1997 (DE) .......................................... 197 39 372
Aug. 21, 1998 (DE) .......................................... 198 37 997

(51) Int. Cl.[7] .................................................. A61F 2/12
(52) U.S. Cl. .......................................... 623/7; 264/222
(58) Field of Search .......................... 623/7, 8; 450/57; 264/222

(56) References Cited

U.S. PATENT DOCUMENTS

| 4,466,936 | A | * | 8/1984 | Schapel | ........................ 264/225 |
| 4,600,551 | A | * | 7/1986 | Erb | ............................. 264/222 |
| 4,906,423 | A | * | 3/1990 | Frisch | .......................... 264/48 |
| 5,035,758 | A | * | 7/1991 | Degler et al. | .................. 156/61 |
| 5,370,688 | A | * | 12/1994 | Schultz et al. | .................. 623/7 |
| 5,733,335 | A | * | 3/1998 | Ishikawa et al. | ................ 623/7 |
| 5,824,075 | A | * | 10/1998 | Thielbar | .......................... 623/7 |
| 6,042,608 | A | * | 3/2000 | Ishikawa et al. | ................ 623/7 |
| 6,086,801 | A | * | 7/2000 | Eaton | ......................... 264/40.1 |
| 6,136,027 | A | * | 10/2000 | Jackson | .......................... 623/7 |

* cited by examiner

Primary Examiner—Corrine McDermott
Assistant Examiner—Suzette J. Jackson

(57) ABSTRACT

The invention relates to a method for manufacturing an epithesis, including the following steps: making a plastic shell using a two-piece mould realized based on a body impression, said shell being provided with apertures to be filled; possibly hardening of the shell in the mould; filling the shell with material in the mould; closing the shell and demoulding.

10 Claims, No Drawings

METHOD FOR MANUFACTURING AN EPITHESIS

The invention relates to an epithesis, which is made up of a casing adapted to the body at the rear and at the front is assimilated to the desired body surface, and of a filling in the casing and furthermore to a kit for the performance of the method and for the production of such epitheses.

Epitheses for the compensation of innate or acquired defects of the body have long been known and copiously described. They are employed on a large scale to conceal the consequences of accidents or of surgical operations and to imitate a natural body surface. A frequent purpose of use is the imitation of the female breast after surgical amputation owing to malignant tumors.

In this respect epitheses serve on the one hand to protect the defective body surface against undesired external influences, that is to say for example to aid in wound healing and to improve hygiene. On the other hand epitheses are prescribed and worn more particularly for cosmetic reasons.

Having regard to the intended purpose it is necessary to adapt the epithesis in an optimum fashion to the body surface. This is so because it is only in this manner that basic medical and hygienic requisites may be fulfilled and because it is only so that optimum "wearing comfort" may be guaranteed. A further point is that it is only a well fitted epithesis that creates the desired appearance and allows the patient to move freely. Optimum imitation of the natural body surface, including imitation of the natural skin color, is in this case is an obvious requirement.

Conventional epitheses comprise an outer casing, which is adapted to the body surface and is filled with a liquid. The material of the casing normally consists of silicone rubber or also a polyurethane plastic, such substances having been shown to extremely compatible with the skin. Frequently, the filling consists of a liquid silicone.

Disadvantages encountered with such known epitheses are however the ability to flow and the poor dimensional stability of the filling. This leads to the necessity of appropriate measures for the attachment of the epithesis, which accordingly must be more complex than is compatible with wearer comfort. This, and the relatively high concomitant weight, leads to impairments as regards mobility and, in the case of vigorous movements, to a proneness of the epithesis to slip out of position. Moreover there is the danger of leakage following any damage to the casing. Air-filled epitheses collapse, if the casing is punctured.

A further disadvantage of known epitheses is their low degree of adaptation to individual needs. Standardized epitheses are only occasionally able to meet the requirements of an individual case. Optimum adaptation to the body surface and to the general appearance of the wearer are however essential for wearer comfort and acceptability.

One object of the invention now is to provide an epithesis and means, which while avoiding the above disadvantages are satisfactory from the medical point of view, are compatible with the skin—in the event of leakage of the filling or puncture of the casing—and which result in an epithesis possessing the elasticity and dimensional stability/yielding properties of the natural skin surface. Moreover the epithesis is to keep its shape over long periods of time. More especially, individual adaptation of the epithesis to features of the body of the wearer is to be rendered possible.

This object is to be attained by a method comprising the following steps:
  production of a casing of a plastic material using a two-part mold and of an impression of the body, said casing having openings as necessary for filling same,
  if necessary, curing of said casing in the mold,
  filling of the casing with filling material in the mold,
  closing the casing, and
  demolding.

The invention also relates to an epithesis, which comprises a casing manufactured of plastic material, which to the rear is adapted to a part of the body and at the front imitates the desired body surface, and furthermore a filling for the casing, said filling comprising a gel of gelatine dissolved in water.

Epitheses produced in accordance with the invention and also epitheses in accordance with the invention comprise a casing and a filling. The casing comprises a plastic material, which is manufactured using a two-part mold and an impression taken from the body, such impression permitting an exact adaptation of the rear side of the epithesis to the body of the wearer. The casing so produced possesses at least one opening as necessary for the filling with the filling material and closed with a plug.

For manufacture of the casing it is possible to employ a prefabricated mold or a template, which is filled like an impression tray with an impression composition, such as an alginate, to take the contour of the rear part of the mold from the body surface of the wearer. The template itself is a representation of the outer or visible part of the epithesis. The impression of the body surface is imparted to a plastic foil, which then represents the second, rear part of the mold. As materials coming into question for the mold it is possible to utilize plastics and more particularly polyester as for example PET.

For the manufacture of the casing the mold is more particularly employed in the form of a negative mold. For this purpose, after taking the impression, the impression material in the mold is removed and the two parts of the mold are joined together. It is convenient for at least one opening to be provided in the mold, such opening also being continued in the casing to be produced in the mold. This opening is necessary on the one hand for filling the mold with the composition for the casing and also for filling the eventually formed casing with the filling material of the epithesis. In the case of breast epitheses such opening will conveniently be located at the mammary papilla.

For producing the casing the interior of the mold is coated with a curable plastic material, as for instance with a thickness of about 1 mm, which then cures to give the casing. As a material for this it is more especially possible to utilize silicone and polyurethane. Furthermore it is possible to employ deep drawable plastic foils, which are laid in the mold and drawn.

To the extent that such curing of the casing is necessary, such curing will performed in the mold in order to prevent deformation. Curing may take place in a conventional fashion, for example by heating, chemically or by suitable irradiation.

After the production of the casing same is filled in the mold with the respectively desired filling material. Filling in the mold will serve to prevent any deformation. As filling materials foamable materials and gels primarily come into question. Then the casing is sealed and removed from the mold.

It will be clear that the plastic compositions used for forming the casing will be colored to met requirements.

Of the two-part mold, which is employed for the manufacture of the epithesis, it is possible for the front part to be reused.

More particularly preferred materials for filling the casing are plastic foams, as for instance foam of silicone plastic or polyurethane. Preferably the same material is employed for the foam as for forming the casing as well. It is in this manner that cross linking linking of the foam filling with the casing may be ensured. Foam filled epitheses are described in the European patent publication 0 815 811 A.

An important point is that the physical properties. of the filling are set to be elastic, is able to yield to pressure to a certain degree without this leading to the epithesis slipping out of position.

It has been found that more particularly gels are suitable which may be introduced into the casing and are able to yield under pressure and owing to lateral displacement transfer a part of the pressure to the side but afterwards, dependent on the physical properties, return more or less rapidly into their normal condition. Consequently a filling is also more particularly suitable which consists of an aqueous gelatine solution. Such a filling yields under pressure. Furthermore, silicone gels are particularly suitable.

It will be clear that other suitable gel-forming materials may be utilized, as for example those on the basis of aqueous solutions or dispersions of silicic acid, montmorillonites, bentonites, polysaccharides, pectins and the like.

Particularly preferred are also lyogels, which liquefy under pressure or on heating and then solidify again. This is an advantage both for the production of the epitheses and also for their performance.

The material of the casing may more particularly consist of a skin-compatible, medically tested silicone rubber, which is able to be colored and is commercially available. Typically the rubber will have a durometer of 20 Shore A. A satisfactory material is for example supplied by the Orthomax Company, UK. Furthermore polyurethane plastics and polyethylene terephthalate are suitable, as are supplied, f. i. by the Erkodent Company, Mannheim, Germany, under the designations Erkodur and Erkoflex.

To the extent that epitheses produced in accordance with the invention possess a foam filling, they will have a low weight coupled with dimensional stability and, simultaneously, flexibility and elastic recovery into the original shape. Since no liquid filling is present, leakage is not possible, as may for instance otherwise occur as the result of long years of use or owing to mechanical loads in the case of conventional epitheses, it is equally impossible for the epithesis to collapse, as is the case of with known air-filled "floating protheses". For gel-filled epitheses this will apply if the weight is reasonable; the tendency to leak is greatly reduced by the use of gel.

The epitheses produced in accordance with the invention and epitheses in accordance with the invention are primarily employed for the correction of the appearance of the female breast following an operation. They may however also be employed on other parts of the body, as for example in the gluteal region, the waist or the calves. Breast epitheses are conveniently worked into bras, corsets or swim suits so as to ensure a good fit.

The invention furthermore contemplates the casing of a breast epithesis, which is adapted to be filled with a gel or a foam plastic composition, for which purpose it possesses an opening generally at the mammary papilla and which after filling can be sealed off with an imitation nipple.

Lastly the invention relates to a kit for the performance of the method of the invention and for the manufacture of epitheses in accordance with the invention, which comprises one or more standardized or customized templates for making casings adapted to a part of the body from a plastic material together with a plastic composition suitable for the casings and a material for the filling.

The templates, which preferably imitate the relevant part of the body in a plurality of designs, are not yet adapted. From the item, which is respectively selected for the production of the epithesis, a copy is firstly produced in wax or plastic, adapted and then has a negative mold, for example of plaster of Paris, made from it. Using the negative mold with the respective plastic material the epithesis casing or, respectively, in the case of the nose, ears and eyes, the entire epithesis is formed as an imitation using the plastic material.

In like manner it is possible to produce standardized and/or individually customize finger epitheses, PET preferably being utilized as a material, which is particularly suitable as regards cleaning. Finger epitheses may also be mounted on a pin anchored in the finger stump, something which in addition to satisfactory adaptation ensures excellent mobility and gripping performance.

In the case of a kit for breast epitheses the templates are for example standard models in accordance with accepted bra sizes, for example in the sizes A through D.

In accordance with a particular possibility application the templates are designed in the form of impression trays, which are used to take the contour of the body surface, on which the epithesis is to the placed. For this purpose the kit will comprise a conventional impression composition, for example on an alginate basis. The impression is then employed to imitate the body surface on the basis of a plastic composition or foil. After removal of the impression material the template and the deformed foil are united to give a mold, which may then be utilized for forming the epithesis casing. For this purpose the template preferably possesses an opening—in the case of a kit for producing breast epitheses—at the mammary papilla, through which the interior of the mold may be coated plastic. able to be cured or drawn in. After curing the casing, or, respectively, placing it in the mold and while still in the mold, the interior of the casing is filled with the filling material and then sealed.

Such sealing operation is in the case of breast epitheses performed by bonding on the mammary papilla. In this case the template serves both as a positive and as a negative mold.

In addition to the above mentioned parts the kit in accordance with the invention may also comprise pigments and color scales for matching the epithesis to the shade of the skin. Preferably the plastic material employed for the casing is pre-tinted or pre-colored so that only an intensification or a reduction of the basic coloration must be performed. Furthermore the kit may comprise, if it is intended for the production of breast epitheses, imitations of mammary papillas, which are bonded to the casing produced, possibly for sealing the filling opening as well. Here as well later adjustment of the pigmentation may take place.

The templates employed in the kit in accordance with the invention will as a rule be produced in accordance with idealized models and as already noted will be best made available in a plurality of sizes. The open rear side of such templates permits an individual adaptation to the respective wearer with the aid of an impression composition. The template accordingly serves as an impression tray, which with the impression taken may be converted into the finished epitheses in a central or in-house lab. Accordingly the kit renders possible an individual adaptation of the epithesis produced with it to the wearer and ensures an optimum fit and wearer comfort for the epitheses produced with it.

What is claimed is:

1. A method for the manufacture of a breast epithesis, comprising the following steps:

forming a casing by deep-drawing a plastic material using a two-part mold formed from an impression taken of a body, said casing having an opening for filling thereof in a papillar region;

curing said casing in the mold;

filling the casing with an aqueous gel in the mold;

sealing the opening with a papillar prosthesis member; and demolding.

2. The method as claimed in claim 1, wherein the mold is a negative mold.

3. The method as claimed in claim 1, wherein the plastic material is a silicone or polyurethane plastic.

4. The method as claimed in claim 1, wherein the plastic material is polyethylene terephthalate foil.

5. The method as claimed in claim 1, wherein the casing is filled with gelatine dissolved in water.

6. The method as claimed in claim 1, wherein the opening is sealed with the papillar prosthesis member by bonding to the surrounding casing material.

7. A breast epithesis, comprising a casing manufactured from a deep-drawn plastic material, which to the rear is adapted to the body part and at the, front imitates the desired body surface; a filling in the casing including a gel of gelatine dissolved in water; and an opening in a papillar region thereof through which the filling is introduced into the casing and that is sealed by a papillar prosthesis member.

8. The breast epithesis as claimed in claim 7, wherein the casing includes a skin-compatible silicone rubber or polyurethane plastic, or a polyethylene terephthalate foil.

9. A kit for producing an epithesis, comprising:

means for forming a casing including at least one design template adapted to a body part and a plastic composition for the casing;

filling material to be introduced into the casing; and at least one papillar prosthesis member, wherein the at least one design template is in the form of impression, the means for forming the casing includes an impression composition and a permanently deformable plastic foil.

10. The kit as claimed in claim 9, further comprising pigments and color scale.

* * * * *